(12) United States Patent
Kesler

(10) Patent No.: US 11,626,032 B2
(45) Date of Patent: Apr. 11, 2023

(54) METHODS AND DEVICES FOR INCREASING URINE STREAM ACCURACY

(71) Applicant: Kris Kesler, Phoenix, AZ (US)

(72) Inventor: Kris Kesler, Phoenix, AZ (US)

(73) Assignee: KRIS KESLER, Phoenix, AZ (US)

( * ) Notice: Subject to any disclaimer, the term of this patent is extended or adjusted under 35 U.S.C. 154(b) by 338 days.

(21) Appl. No.: 16/805,357

(22) Filed: Feb. 28, 2020

(65) Prior Publication Data
US 2020/0279504 A1 Sep. 3, 2020

Related U.S. Application Data

(60) Provisional application No. 62/812,336, filed on Mar. 1, 2019.

(51) Int. Cl.
*G09B 19/00* (2006.01)
*G01N 31/22* (2006.01)

(52) U.S. Cl.
CPC ....... *G09B 19/0076* (2013.01); *G01N 31/221* (2013.01)

(58) Field of Classification Search
CPC ...... G09B 19/0076; A47K 3/00; A47K 11/00; A47K 17/00; A63H 23/00
See application file for complete search history.

(56) References Cited

U.S. PATENT DOCUMENTS

| 2013/0061384 A1* | 3/2013 | Robertson | E04H 4/14 4/496 |
| 2013/0157236 A1* | 6/2013 | Yang | G09B 19/0076 434/247 |
| 2015/0250284 A1* | 9/2015 | Gonzalez, Jr. | A45D 7/045 132/200 |

FOREIGN PATENT DOCUMENTS

| JP | H11207045 A | * | 8/1999 | |
| JP | 2006020794 | * | 7/2004 | A47K 3/00 |

* cited by examiner

*Primary Examiner* — Robert J Utama
(74) *Attorney, Agent, or Firm* — K&L Gates LLP

(57) ABSTRACT

A floating device acting as a target for enhancing the accuracy of a urine stream. When placed inside a toilet bowl, the target provides visual stimulation and cognitive reinforcement in response to contact with urine. The target may comprise a hull with a cavity. A reactive substance may be placed in the cavity of the hull. The reactive substance may provide a visual stimulation or cognitive reinforcement when contacted by the urine stream. A top portion may be fit against the hull to retain the reactive substance in the cavity of the hull. A barrier layer may cover at least a portion of the hull and/or the top portion. The barrier layer may be semi-permeable or selectively permeable to water when contacted by a urine stream from a user.

19 Claims, 6 Drawing Sheets

METHODS AND DEVICES FOR INCREASING URINE STREAM ACCURACY

CROSS-REFERENCE TO RELATED APPLICATION

This application claims the benefit of priority from U.S. Provisional Application 62/812,336, filed under the same title on Mar. 1, 2019, the entire contents of which are incorporated herein by reference.

TECHNICAL FIELD

The present invention relates, generally, to floating devices for enhancing the accuracy of a urine stream and, more particularly, to a target, such as a training toy, which, when placed inside a toilet bowl, provides visual stimulation and cognitive reinforcement in response to contact with the urine stream.

BACKGROUND

Popular methodologies for toilet training (or "potty" training) children generally include: i) the "Child-Oriented" (CO) or "Brazelton" approach developed by renown pediatrician Dr. T. Berry Brazelton in the 1960's; ii) the Two-Day (or three-Day) Method developed in the 1970's by behavioral psychologists Nathan Azrin and Richard Foxx and popularized in their best-selling book Toilet Training In Less Than A Day; and iii) the default "Let Your Child Train Himself" method. These methods effectively address the psychological aspects of potty training, but are not well suited to improve the aim of young boys, particularly when standing up.

Various decals, splash guards, and stationary and floating targets designed to direct the urine stream towards the center of the toilet bowl are also widely available.

Presently known devices are unsatisfactory, however, in that they lack sufficient visual stimulation to capture and maintain the attention of boys (and men) for the entire duration of a urination event.

Systems and methods are thus needed which overcome the limitations of the prior art.

Various features and characteristics will also become apparent from the subsequent detailed description and the appended claims, taken in conjunction with the accompanying drawings and this background section.

BRIEF SUMMARY

The present invention provides devices and associated methods for encouraging a male to direct his urine stream towards the center of the urinal or toilet bowl. Various embodiments employ a target configured as a battle ship or other familiar (or abstract) structure which chemically reacts with the urine stream to produce visual and/or aural effects to maintain the user's focus on the device while urinating. The complexity of the device's configuration, the volatility of the chemical reaction, the amplitude of the noise and/or colors created thereby, and the length of the chemical and mechanical transformation of the device, and/or other gamification themes may be employed to optimize the user experience.

It should be noted that the various inventions described herein, while illustrated in the context of potty training, are not so limited. In accordance with further embodiments of the invention, the device may be used to train or re-train individuals to minimize splashing and errant sprays, for example in the context of PTSD, disabilities induced by trauma, developmentally disabled persons, individuals struggling with Alzheimer's, autism, Asperger's syndrome, or to facilitate physical rehabilitation following sports injuries and accidents.

Various other embodiments, aspects, and features are described in greater detail below.

BRIEF DESCRIPTION OF THE DRAWING FIGURES

Exemplary embodiments will hereinafter be described in conjunction with the appended drawing figures, wherein like numerals denote like elements, and:

DETAILED DESCRIPTION OF PREFERRED EXEMPLARY EMBODIMENTS

Figure 1:
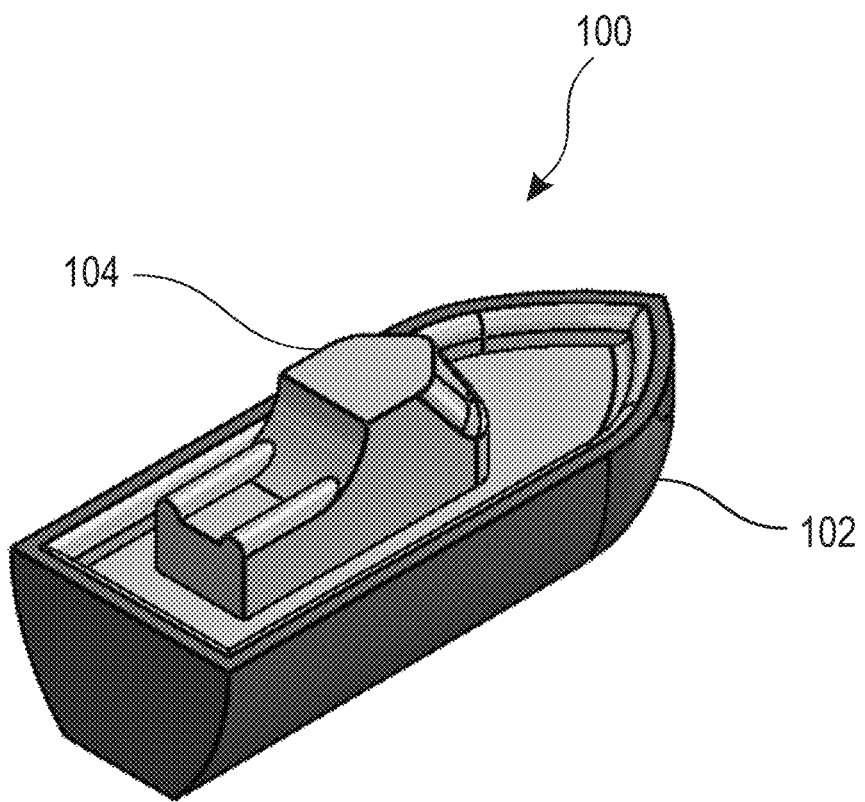
FIG. 1 is a perspective schematic rendering of a floating battle ship target toy according to various embodiments.

The following detailed description of the invention is merely exemplary in nature and is not intended to limit the invention or the application and uses of the invention. Furthermore, there is no intention to be bound by any theory presented in the preceding background or the following detailed description.

In one embodiment, a floating device may be used as a target 100 that comes apart when exposed to, or contacted by, a urine stream. Various embodiments of the present invention relate to systems and methods for reducing splashing, spotting, and misdirected sprays during urination by directing the user's focus—and his urine stream—onto the floating target 100 inside the toilet bowl or urinal. To help maintain the user's focus on the target 100, the device may be made from materials which react with the urine stream to created visual and/or aural effects such as, for example, crackling, the appearance of smoke, and the emission of color and/or sound.

Various embodiments contemplate a target device 100 totally or at least partially surrounding by a thin barrier layer 502 enclosing a reactive substance. When floating in a toilet bowl, the barrier layer 502 prevents the reactive substance from contacting the surrounding water. When contacted by urine, the barrier layer 502 may decompose, break down, become unattached to a surface of the target 100 or otherwise allow water (and urine) to contact the reactive substance to produce the desired visual and/or aural effects.

The chemical and mechanical response of the barrier layer 502 and/or the reactive substance to the urine stream may be predicated on a reaction between or among one or more components of the target 100 and one or more components of the urine. Alternatively or in addition to the foregoing, the target 100 may embody one or more of the following features: i) a membrane which is semi-permeable or selectively permeable to water, that is, water can selectively penetrate an outer barrier in the presence of a component of urine; ii) a membrane, region, switch, or surface coating (fully or partially covering a surface) which responds to a pressure and/or temperature threshold value or differential (where urine is in the range of 90°-98° F. and the toilet water is in the room temperature range); and iii) a barrier layer or surface feature which reacts in response to a change in pH value or other chemical parameter.

In this regard, human urine consists primarily of water (91% to 96%), with organic solutes including urea, creatinine, uric acid, and trace amounts of enzymes, carbohydrates, hormones, fatty acids, pigments, and mucins, and inorganic ions such as sodium (Na+), potassium (K+), chloride (Cl−), magnesium (Mg2+), calcium (Ca2+), ammonium (NH4+), sulfates (SO42−), and phosphates (e.g., PO43−).

A typical sample of human urine comprises the following chemical composition: i) 95% water (H2O); ii) 9.3 g/l to 23.3 g/l Urea (H2NCONH2); iii) 1.87 g/l to 8.4 g/l Chloride (Cl−); iv) 1.17 g/l to 4.39 g/l Sodium (Na+); iv) 0.750 g/l to 2.61 g/l Potassium (K+); v) 0.670 g/l to 2.15 g/l Creatinine (C4H7N3O); and vi) 0.163 to 1.80 g/l Inorganic sulfur (S). Lesser amounts of other ions and compounds may also be present, including hippuric acid, phosphorus, citric acid, glucuronic acid, ammonia, and uric acid.

The pH of human urine ranges from 5.5 to 7, averaging around 6.2. The specific gravity ranges from 1.003 to 1.035. Significant deviations in pH or specific gravity may be attributable to diet, drugs, or urinary disorders.

A normal "pee first thing in the morning" quantity is typically in the range of 8-16 ounces for an adult, and correspondingly less for children. Healthy daytime voids are around 6-10 ounces each. The quantity of material comprising the target 100 may thus be configured to accommodate a single use, multiple uses, or tuned to a pre-determined quantity of urine. That is, potty training targets 100 may embody a significantly smaller quantity of reactive substances than a novelty target 100 for adult use.

A Fizzy Frigate gives young male children and full grown adult males (and perhaps some enterprising girls and curious women) something in the toilet to aim at while vacating the user's bladder. Consequently, bathroom facilities may be kept clean, sanitary, and free of stains. The Fizzy Frigate may take the form, as a non-limiting example, of a little boat that when gently placed in the toilet water and intentionally urinated on will proceed to go into motion, fizzle, pop n' crackle, discolor the water, dissolve, sparkle with effervescence, and thereafter sink and perhaps even create a tiny oil slick. This technique can help focus the user's attention and visual acuity on the target 100, while enhancing hand-to-eye coordination. A participant's aim thus becomes more intentional and, over time, more accurate. Indeed, improved accuracy may be sustained over subsequent urination events even without the use of a target 100. The stress of the urinary experience and associated mess is steadily reduced through continued use of a floating toilet target 100.

Chemical Composition and Construction

In an embodiment, in a low humidity environment, the hull 102 of the target 100 may be made from chemical components. As a non-limiting example, the chemical components may be between 0.5 and 1.5 part sodium bicarbonate powder, between 0.5 and 1.5 part powdered crystalline citric acid, between 0.5 and 1.5 part cornstarch and between ¼ and 1/64 part vegetable oil, by weight or by volume.

In another embodiment, the chemical components of the hull 102 of the target 100 may be between 0.75 and 1.25 part sodium bicarbonate, between 0.75 and 1.25 part powdered crystalline citric acid, between 0.75 and 1.25 part cornstarch and between ⅛ and 1/32 part vegetable oil by weight or volume.

In another embodiment, the chemical components of the hull 102 of the target 100 may be approximately one part sodium bicarbonate powder, approximately one part powdered crystalline citric acid, approximately one-fourth part cornstarch, and approximately 1/16 part vegetable oil, by weight or by volume.

The chemical components may be mixed together thoroughly, then lightly spray-moistened and mixed again until the ingredients can be compressed together softly.

The mixture may then be placed in a mold of any desired shape and size (e.g., the hull 102 of a small boat), and hydraulically or pneumatically compressed into a hull 102, preferably with a cavity. The hull 102 is hereby defined to be a bottom portion of a target 100 of any shape or size and is not necessarily limited to a bottom portion of a boat. In preferred embodiments, the hull 102 displaces an amount of toilet water equal to the weight of the target 100, thereby allowing the target 100 to float in the toilet bowl.

Carbonated crystals, aka "pop rocks", may be placed inside the cavity of the hull 102. Then a molded top portion 104 of the boat may be used to seal in the contents. In an embodiment, beeswax is used to make the seal.

The hull 102 of the Fizzy Frigate may also be lightly coated with aerosol wax, preventing the premature breakdown of the structure coupled with increased buoyancy until the urinary process begins.

For interesting visual effects, a variety of colorful vessel markings may be printed on dissolvable paper (sodium carboxyl methyl cellulose) and adhered to the target 100. All components are preferably biodegradable and non-toxic.

Gradually flared, tapered or convex surfaces may be employed to avoid outspraying, reduce splatter, and otherwise contain secondary urine splashing off the target 100. The structure should minimize or avoid sharp edges, corners, low radius, and concave features which tend to deflect urine upwardly.

Adult Version

The internal contents of an adult version may further include miniscule sodium metal pellets, magnesium granules, and/or potassium metal fragments. When urinated upon and exposed to water, these materials may (or may appear to) ignite, smoke, spark, and/or lightly combust before sinking. Silica gel beads may also be used for moisture absorption prior to urine catalyzed ignition. Other internal components as well as by-products of the target's destruction may be generally analogous to common drain cleaning products.

FIG. 1 depicts an exemplary target 100 comprising a boat hull 102, surface features and a top portion 104.

Figure 2:
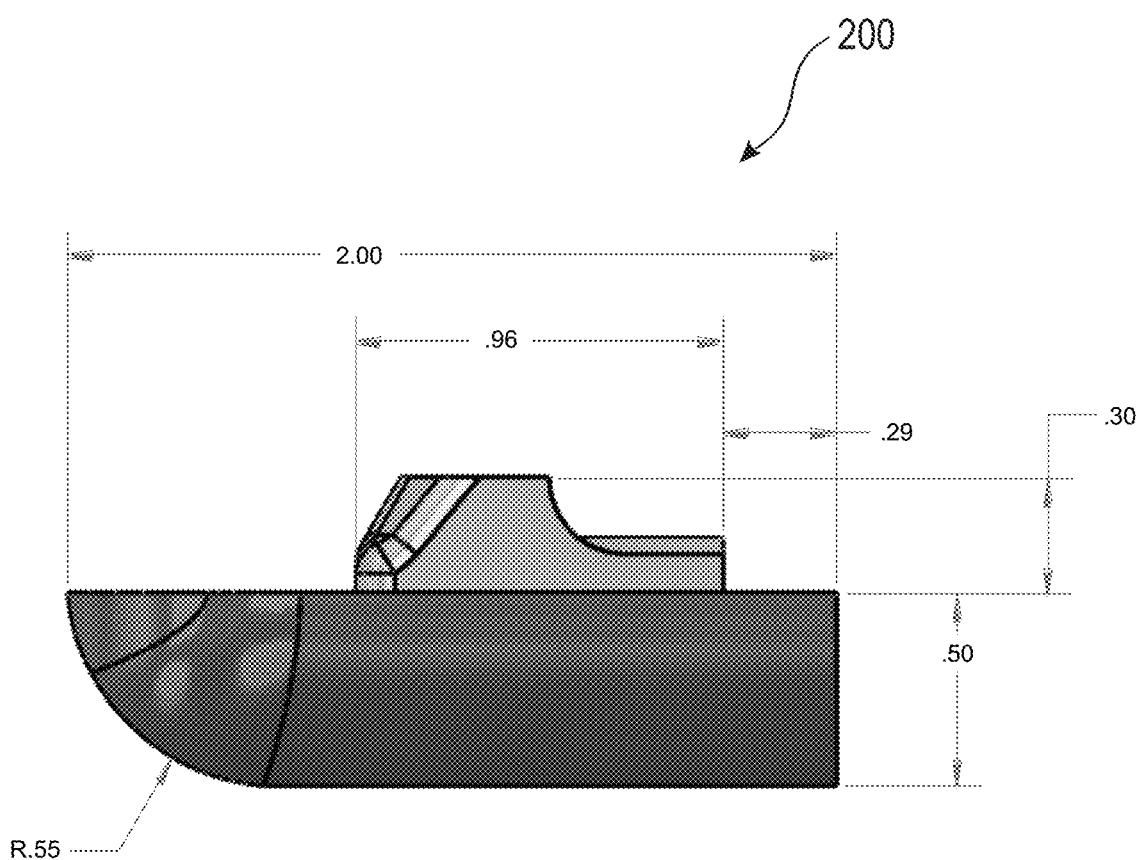
FIG. 2 is a side elevation view of the target of FIG. 1 according to various embodiments.

FIG. 2 depicts an exemplary target 200 exhibiting various nominal dimensions.

Figure 3:
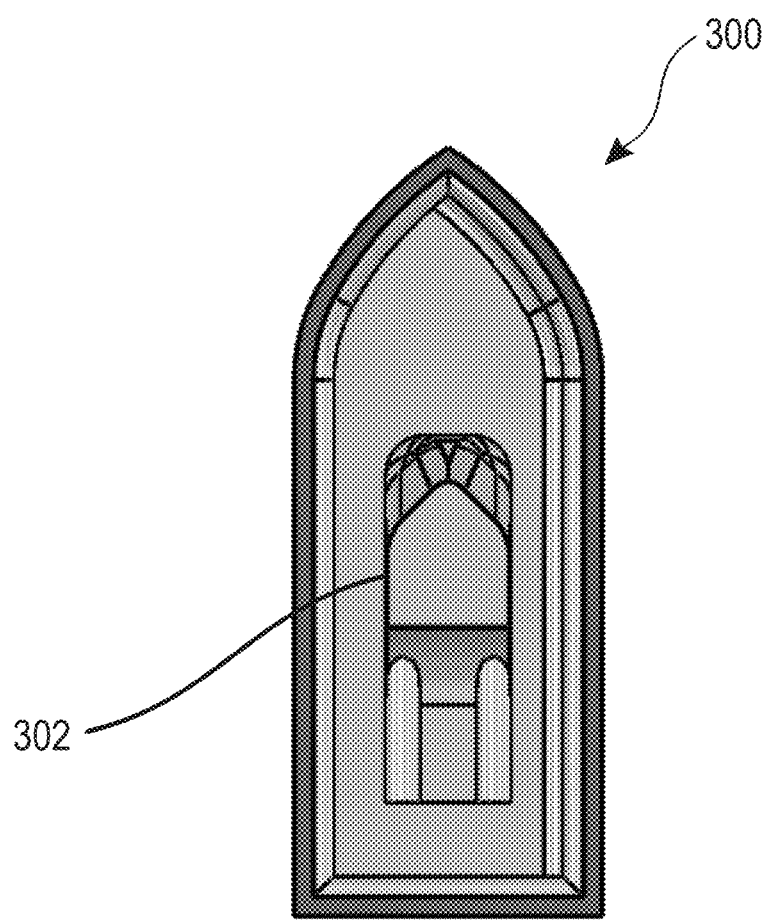
FIG. 3 is a top plan view of the target of FIG. 1 according to various embodiments.

FIG. 3 depicts an exemplary target 300 including various surface features 302.

Figure 4:
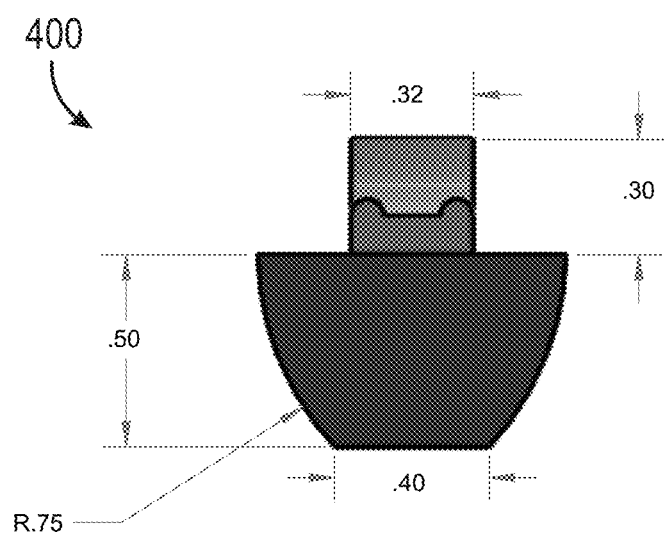
FIG. 4 is an end view of the target of FIG. 1 according to various embodiments.

FIG. 4 is an end view of an exemplary target 400 exhibiting various nominal dimensions.

Figure 5:
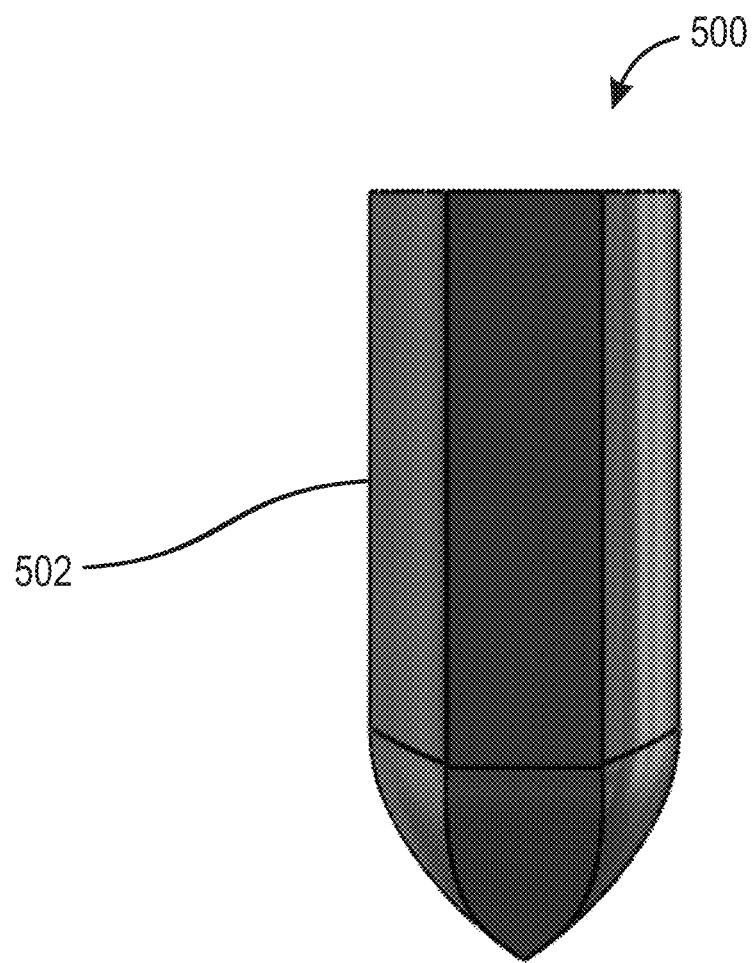
FIG. 5 is a bottom view of the target of FIG. 1 according to various embodiments.

FIG. 5 is a bottom view of an exemplary target 500 having a barrier layer 502 comprising a non-water permeable, semi-permeable, or selectively permeable membrane.

Figure 6:
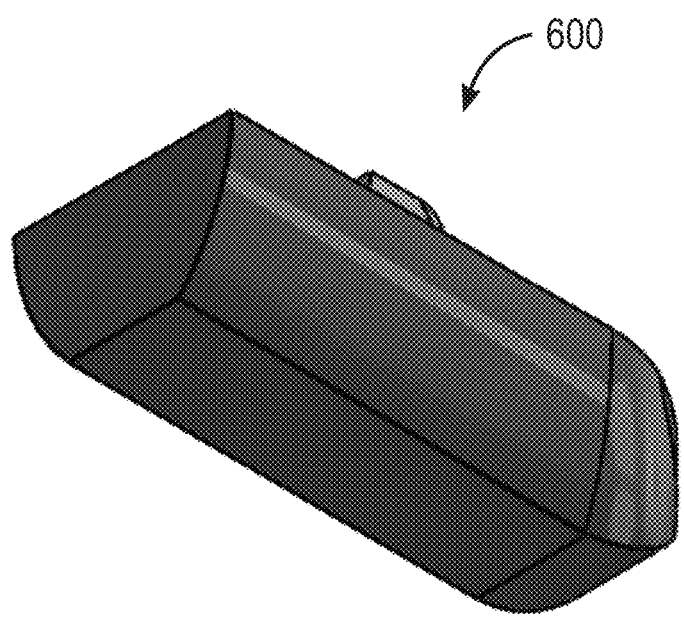
FIG. 6 is a bottom perspective view of the target of FIG. 1 according to various embodiments.

FIG. 6 is a bottom perspective view of an exemplary target 600.

While the target 100 has generally been described as being in the shape of a boat, i.e., the Fizzy Frigate, it should be appreciated that the target 100 may be of any desired shape or form. As non-limiting examples, the target 100 may depict and/or be in the shape of an animal, person or any other desired geometric shape or object.

In another embodiment, a target 100 capable of floating in a toilet bowl to assist in enhancing an accuracy of a urine stream into the toilet bowl from a user may comprises four different elements.

First, the embodiment may include a hull 102 that includes a cavity. The hull 102 is configured to displace an amount of toilet water that is equal in weight to the target 100. In some embodiments the hull 102 may be coated with a wax. In some embodiments the hull 102 comprises approximately 1 part sodium bicarbonate powder, approximately 1 part powdered crystalline citric acid, approximately 1 part cornstarch and approximately $\frac{1}{16}$ part vegetable oil, by weight or by volume. In some embodiments, dissolvable paper comprising sodium carboxyl methyl cellulose may be adhered to the hull 102 and/or the top portion 104 of the target 100.

Second, the embodiment may include a reactive substance placed in the cavity of the hull 102. The reactive substance may be one or more of carbonated crystals, sodium metal pellets, magnesium granules and/or potassium metal fragments.

Third, the embodiment may include a top portion 104 of the target 100 configured to fit against the hull 102 to retain the reactive substance in the cavity of the hull 102.

And fourth, the embodiment may include a barrier layer 502 configured to separate from the surface of the hull 102 and/or the surface of the top portion 104 when the urine stream from the user contacts the barrier layer 502.

The barrier layer 502 may be a semi-permeable or selectively permeable to water in a presence of a component of urine in the urine stream.

The barrier layer 502 may be configured to come off of the hull 102 and/or the top portion 104 due to a pressure and/or a temperature threshold value or differential with the toilet water caused by the urine stream from the user.

The barrier layer 502 may be configured to come off of the hull 102 and/or the top portion 104 in response to a change in pH value or other chemical parameter in the toilet bowl caused by the urine stream from the user.

As used herein, the word "exemplary," "example" or "embodiment" means "serving as an example, instance, or illustration." Any implementation so described herein is not necessarily to be construed as preferred or advantageous over other implementations, nor is it intended to be construed as a model that must be literally duplicate.

While the foregoing detailed description will provide those skilled in the art with a convenient road map for implementing various embodiments of the invention, it should be appreciated that the particular embodiments described above are only examples, and are not intended to limit the scope, applicability, or configuration of the invention in any way. To the contrary, various changes may be made in the function and arrangement of elements described without departing from the scope of the invention.

What is claimed is:

1. A target capable of floating in a toilet bowl to assist in enhancing an accuracy of a urine stream into the toilet bowl from a user, comprising:
   a hull including a cavity, wherein the hull is configured to displace an amount of toilet water that is equal in weight to the target, and wherein the hull comprises between 0.75 and 1.25 part sodium bicarbonate powder, between 0.75 and 1.25 part powdered crystalline citric acid, between 0.75 and 1.25 part cornstarch, and between $\frac{1}{8}$ and $\frac{1}{32}$ part vegetable oil, by weight or by volume;
   a reactive substance in the cavity of the hull;
   a top portion of the target configured to fit against the hull to retain the reactive substance in the cavity of the hull; and
   a barrier layer on at least a portion of the hull and/or the top portion, wherein the barrier layer is semi-permeable or selectively permeable to water in a presence of a component of urine.

2. The target of claim 1, wherein the reactive substance comprises carbonated crystals.

3. The target of claim 1, wherein the reactive substance comprises sodium metal pellets.

4. The target of claim 1, wherein the reactive substance comprises magnesium granules.

5. The target of claim 1, wherein the reactive substance comprises potassium metal fragments.

6. The target of claim 1, wherein the hull is coated with a wax.

7. The target of claim 1, wherein dissolvable paper comprising sodium carboxyl methyl cellulose is adhered to the hull and/or the top portion of the target.

8. A target configured to float in a toilet bowl, comprising:
   a hull with a cavity, wherein the hull is configured to displace an amount of toilet water that is equal in weight to the target;
   a reactive substance in the cavity of the hull;
   a top portion of the target configured to engage with the hull to seal the reactive substance in the cavity of the hull; and
   a surface coating covering at least a portion of the hull or the top portion and wherein the surface coating is configured to separate from the hull and/or the top portion due to a pressure and/or a temperature threshold value or differential with the toilet water caused by a urine stream from a user.

9. The target of claim 8, wherein the hull comprises between 0.5 and 1.5 part sodium bicarbonate powder, between 0.5 or 1.5 part powdered crystalline citric acid, between 0.5 and 1.5 part cornstarch and between $\frac{1}{4}$ and $\frac{1}{64}$ part vegetable oil, by weight or by volume.

10. The target of claim 8, wherein the reactive substance comprises at least one ingredient selected from a group consisting of (i) carbonated crystals, (ii) sodium metal pellets, (iii) magnesium granules and (iv) potassium metal fragments.

11. The target of claim 8, wherein the hull is coated with a wax.

12. The target of claim 8, wherein dissolvable paper comprising sodium carboxyl methyl cellulose is adhered to the hull and/or the top portion of the target.

13. A method, comprising the steps of:
   providing a hull with a cavity, wherein the hull is configured to displace an amount of toilet water that assists the target in floating in the toilet bowl;
   placing a reactive substance in the cavity of the hull;
   attaching a top portion of the target to the hull of the target so as to seal the reactive substance in the cavity of the hull; and
   coating a surface of the hull and a surface of the top portion with a barrier layer, wherein the barrier layer is configured to separate from the surface of the hull and/or the surface of the top portion when the urine stream from the user contacts the barrier layer.

14. The method of manufacturing of claim 13, wherein the barrier layer is semi-permeable or selectively permeable to water in a presence of a component of urine in the urine stream.

15. The method of manufacturing of claim 13, wherein the barrier layer is configured to come off of the hull and/or the top portion due to a pressure and/or a temperature threshold value or differential with the toilet water caused by the urine stream from the user.

16. The method of manufacturing of claim 13, wherein the barrier layer is configured to come off of the hull and/or the top portion in response to a change in pH value or other chemical parameter in the toilet bowl caused by the urine stream from the user.

17. The method of manufacturing of claim 13, wherein the hull comprises approximately 1 part sodium bicarbonate powder, approximately 1 part powdered crystalline citric acid, approximately 1 part cornstarch and approximately 1/16 part vegetable oil, by weight or by volume.

18. The method of manufacturing of claim 13, wherein the reactive substance comprises at least one ingredient selected from a group consisting of (i) carbonated crystals, (ii) sodium metal pellets, (iii) magnesium granules and (iv) potassium metal fragments.

19. The method of manufacturing of claim 13, wherein dissolvable paper comprising sodium carboxyl methyl cellulose is adhered to the hull and/or the top portion of the target.

* * * * *